US00PP33647P2

(12) United States Plant Patent
Moeller

(10) Patent No.: US PP33,647 P2
(45) Date of Patent: Nov. 16, 2021

(54) ***AGASTACHE* PLANT NAMED 'DANISH DELIGHT'**

(50) Latin Name: *Agastache hybrida*
Varietal Denomination: Danish Delight

(71) Applicant: FUTURE PLANTS LICENTIE B.V., Lisserbroek (NL)

(72) Inventor: Tina Moeller, Aabybro (DK)

(73) Assignee: FUTURE PLANTS LICENTIE B.V., Lisserbroek (NL)

( * ) Notice: Subject to any disclaimer, the term of this patent is extended or adjusted under 35 U.S.C. 154(b) by 0 days.

(21) Appl. No.: 17/190,845

(22) Filed: Mar. 3, 2021

(51) Int. Cl.
*A01H 5/02* (2018.01)
*A01H 6/50* (2018.01)

(52) U.S. Cl.
USPC ..... Plt./399
CPC ..... *A01H 6/50* (2018.05); *A01H 5/02* (2013.01)

(58) Field of Classification Search
USPC ..... Plt./399
CPC ..... A01H 6/50; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Agastache* plant named 'Danish Delight', characterized by its tall and upright plant habit; vigorous growth habit and rapid growth rate; bright green-colored leaves; relatively long inflorescences with numerous large flowers that are bright reddish purple in color; and good garden performance.

2 Drawing Sheets

Figure 1:
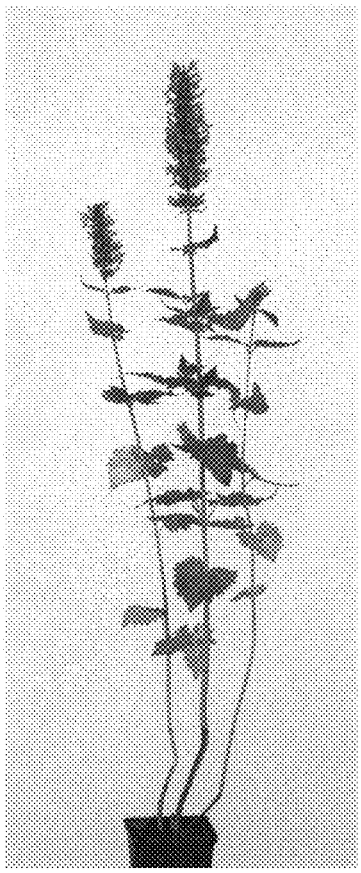

Botanical designation: *Agastache hybrida.*
Cultivar denomination: 'DANISH DELIGHT'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Agastache* plant, botanically known as *Agastache hybrida*, commonly referred to as Giant Hyssop and hereinafter referred to by the name 'Danish Delight'.

The new *Agastache* plant is a product of a planned breeding program conducted by the Inventor in Aabybro, Denmark. The objective of the breeding program is to create new and unique *Agastache* plants.

The new *Agastache* plant originated from a cross-pollination during the summer of 2016 of *Agastache hybrida* 'Blue Boa', disclosed in U.S. Plant Pat. No. 24,050, as the female, or seed, parent with an unnamed proprietary selection of *Agastache hybrida*, not patented, as the male, or pollen, parent. The new *Agastache* plant was discovered and selected by the Inventor as a single flowering plant from within the progeny of the stated cross-pollination in a controlled environment in Aabybro, Denmark during the summer of 2017.

Asexual reproduction of the new cultivar by softwood cuttings in Aabybro, Denmark since the summer of 2018 has shown that the unique features of this new *Agastache* plant are stable and reproduced true to type in successive generations.

SUMMARY OF THE INVENTION

Plants of the new *Agastache* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Danish Delight'. These characteristics in combination distinguish 'Danish Delight' as a new and distinct *Agastache* plant:

1. Tall and upright plant habit.
2. Vigorous growth habit and rapid growth rate.
3. Bright green-colored leaves.
4. Relatively long inflorescences with numerous large flowers that are bright reddish purple in color.
5. Good garden performance.

Plants of the new *Agastache* can be compared to plants of the female parent, 'Blue Boa'. Plants of the new *Agastache* differ primarily from plants of 'Blue Boa' in the following characteristics:

1. Plants of the new *Agastache* are taller than plants of 'Blue Boa'.
2. Plants of the new *Agastache* have bright reddish purple-colored flowers whereas plants of 'Blue Boa' have deep purple blue-colored flowers.

Plants of the new *Agastache* can be compared to plants of the male parent selection. Plants of the new *Agastache* differ primarily from plants of the male parent selection in the following characteristics:

1. Plants of the new *Agastache* have thicker and stronger stems than plants of the male parent selection.
2. Plants of the new *Agastache* have larger flowers than plants of the male parent selection.
3. Plants of the new *Agastache* have bright reddish purple-colored flowers whereas plants of the male parent selection have blue-colored flowers.

Plants of the new *Agastache* can be compared to plants of *Agastache hybrida* 'Sangria', not patented. In side-by-side comparisons, plants of the new *Agastache* differ primarily from plants of 'Sangria' in the following characteristics:

1. Plants of the new *Agastache* are taller than plants of 'Sangria'.
2. Inflorescences of plants of the new *Agastache* are longer and broader than inflorescences of plants of 'Sangria'.
3. Flowers of plants of the new *Agastache* are bright reddish purple in color whereas flowers of plants of 'Sangria' are dark purple in color.
4. Plants of the new *Agastache* are more winter hardy than plants of 'Sangria'.

Plants of the new *Agastache* can also be compared to plants of *Agastache mexicana* 'Red Fortune', disclosed in U.S. Plant Pat. No. 11,816. In side-by-side comparisons, plants of the new *Agastache* differ primarily from plants of 'Red Fortune' in the following characteristics:

1. Plants of the new *Agastache* are taller than plants of 'Red Fortune'.
2. Inflorescences of plants of the new *Agastache* are shorter and broader than inflorescences of plants of 'Red Fortune'.
3. Flowers of plants of the new *Agastache* are bright reddish purple in color whereas flowers of plants of 'Red Fortune' are purple red in color.
4. Plants of the new *Agastache* are more durable than plants of 'Red Fortune'.

BRIEF DESCRIPTION OF THE PHOTOGRAPHS

The accompanying colored photographs illustrate the overall appearance of the new *Agastache* plant showing the colors as true as it is reasonably possible to obtain in colored reproductions of this type. Colors in the photographs may differ slightly from the color values cited in the detailed botanical description which accurately describe the actual colors of the new *Agastache* plant.

The photograph on the first sheet (FIG. 1) is a side perspective view of a typical flowering plant of 'Danish Delight' grown in a container.

Figure 2:
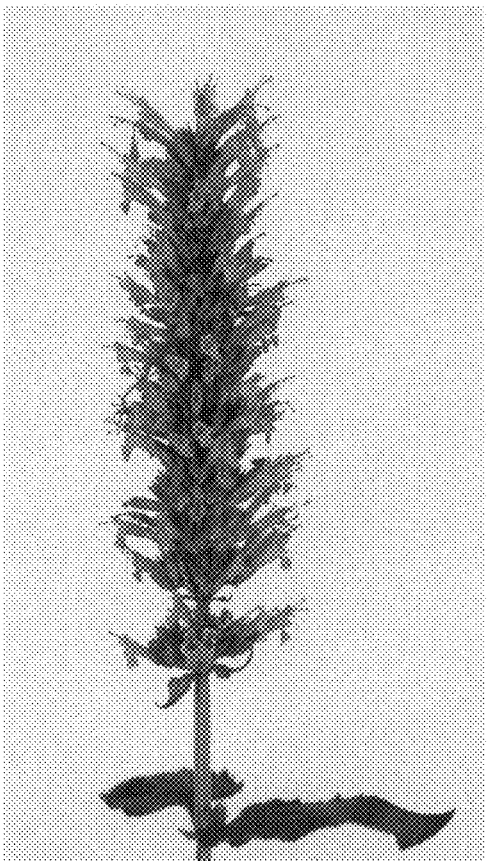

The photograph on the second sheet (FIG. 2) is a close-up view of a typical inflorescence of 'Danish Delight'.

DETAILED BOTANICAL DESCRIPTION

The aforementioned photographs and following observations and measurements describe plants grown during the autumn in 9-cm containers in an outdoor nursery in Lisserbroek, The Netherlands and under conditions and cultural practices which approximate those typically used in commercial *Agastache* plant production. During the production of the plants, day temperatures ranged from 15° C. to 24° C. and night temperatures ranged from 5° C. to 15° C. Plants were one year old when the photographs and description were taken. In the following description, color references are made to The Royal Horticultural Society Colour Chart, Sixth Edition, 2015, except where general terms of ordinary dictionary significance are used. Measurements represent averages for typical flowering plants.

Botanical classification: *Agastache hybrida* 'Danish Delight'.

Parentage:

*Female, or seed, parent.*—*Agastache hybrida* 'Blue Boa', disclosed in U.S. Plant Pat. No. 24,050.

*Male, or pollen, parent.*—Unnamed proprietary selection of *Agastache hybrida*, not patented.

Propagation:

*Type.*—By softwood cuttings.

*Time to initiate roots, summer.*—About 18 days at temperatures about 18° C.

*Root description.*—Medium in thickness, fibrous; typically white to brown in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a container and garden plant; tall and upright plant habit; vigorous growth habit and rapid growth rate.

*Branching habit.*—Basal branching with about three primary lateral branches developing per plant; pinch will enhance lateral branch development.

*Plant height, soil level to top of foliar plane.*—About 62.4 cm.

*Plant height, soil level to top of floral plane.*—About 80.5 cm.

*Plant width.*—About 20.1 cm.

*Primary branch description.*—Length (excluding inflorescence): About 57.4 cm. Diameter: About 4 mm. Internode length: About 7 cm. Shape: Quadrangular. Strength: Moderately strong. Aspect: About 10° from vertical; secondary lateral branches, about 30° from primary branch axis. Texture and luster: Densely pubescent; matte. Color, developing: Close to 144B. Color, developed: Close to 146C; at the ridges, close to 146B.

Leaf description:

*Arrangement.*—Opposite and decussate; simple.

*Length.*—About 8.5 cm.

*Width.*—About 5.8 cm.

*Shape.*—Ovate to narrowly cordate.

*Apex.*—Acuminate.

*Base.*—Cordate.

*Margin.*—Coarsely dentate.

*Texture and luster, upper and lower surfaces.*—Densely pubescent; matte.

*Venation pattern.*—Pinnate.

*Color.*—Developing leaves, upper surface: Close to 197A and N199A. Developing leaves, lower surface: Close to 147B and 148B. Fully expanded leaves, upper surface: Close to 137B; venation, close to 144A. Fully expanded leaves, lower surface: Close to 147B; venation, close to 147D.

*Petioles.*—Length: About 1.9 cm. Diameter: About 1.75 mm by 2 mm. Strength: Moderately strong.

Texture and luster, upper and lower surfaces: Densely pubescent; matte. Color, upper surface: Close to 146C. Color, lower surface: Close to 144C.

Flower description:

*Flower arrangement and shape*.—Single bilabiate flowers arranged on erect and relatively large racemes; freely flowering habit with about 440 flowers developing per inflorescence and about 1,320 flowers developing per plant during the flowering season; flowers face mostly outwardly.

*Fragrance*.—None detected; leaves and stems are sweet and mint-like.

*Natural flowering season*.—Early flowering habit, plants begin flowering about ten weeks after planting; plants flower during the late spring into the summer in an outdoor environment in The Netherlands; flowers last about ten days on the plant, flowers not persistent.

*Flower buds*.—Length: About 1.1 cm. Diameter: About 3.5 mm. Shape: Oblong to narrowly obovate. Texture and luster: Densely pubescent; matte. Color: Immature petals and free sepal apices, close to 53C; immature calyx tube, slightly lighter than N77B.

*Inflorescence height*.—About 11.4 cm.

*Inflorescence diameter*.—About 5.4 cm.

*Flower size*.—About 4 mm by 8 mm.

*Flower depth*.—About 2.4 cm.

*Flower throat diameter*.—About 2 mm.

*Flower tube length*.—About 1.2 cm.

*Flower tube diameter*.—About 3 mm.

*Petals*.—Arrangement: Five petals; two upper petals (upper lip) with two lateral petals and one lower petal (lower lip); petals fused proximally. Length: Upper petals: About 1.7 cm. Lateral petals: About 1.4 cm. Lower petal: About 1.6 cm. Width: Upper and lateral petals: About 2 mm. Lower petal: About 5 mm. Shape: Upper and lateral petals: Narrowly oblanceolate. Lower petal: Narrowly spatulate to narrowly oblanceolate. Apex: Upper and lateral petals: Irregularly obtuse. Lower petal: Retuse to emarginate. Base, all petals: Lower 75% of petals fuse into a narrow tube. Margin: Upper petals: Entire; not undulate. Lateral petals: Entire; slightly undulate. Lower petal: Entire; moderately undulate. Texture and luster, all petals, upper and lower surfaces: Densely pubescent; matte. Texture and luster, throat: Smooth, glabrous; matte. Texture and luster, tube: Densely pubescent; matte. Color, upper and lateral petals: When opening, upper and lower surfaces: Close to 73A. Fully opened, upper and lower surfaces: Close to NN74C; venation, close to NN74C; color becoming closer to 67B with development. Color, lower petal: When opening, upper surface: Close to NN74C. When opening, lower surface: Close to NN74B. Fully opened, upper surface: Close to NN74C; towards the margins, close to NN74B; venation, close to NN74C and NN74B; with development, color becoming closer to 67A. Fully opened, lower surface: Close to NN74C; venation, close to NN74C; with development, color becoming closer to 67B and towards the margins, close to 67A. Throat: Close to NN74C; venation, close to NN74C. Tube, upper side: Close to N74B; venation, close to N74B. Tube, lower side: Close to NN74C to NN74D; venation, close to NN74C to NN74D.

*Calyx*.—Arrangement: Five sepals fused to form a tubular calyx. Length: About 7.5 mm. Width: About 2.5 mm. Sepal length: About 7.5 mm. Sepal width: About 1.5 mm. Sepal shape: Obovate; 60% of proximal length is fused. Sepal apex: Acute. Sepal margin: Entire. Sepal texture and luster, upper (inner) surface: Smooth, glabrous; slightly glossy. Sepal texture and luster, lower (outer) surface: Densely pubescent; matte. Sepal color: When opening, upper (inner) surface: Close to 197C; towards the apex, close to N77B; venation, close to 197A. When opening, lower (outer) surface: Slightly lighter than N77B. Fully opened, upper (inner) surface: Close to 197C; towards the apex, close to N77B; venation, close to 197A. Fully opened, lower (outer) surface: Close to 147C; towards the base, close to 145D and towards the apex, close to N77B.

*Peduncles*.—Length: About 13.3 cm. Diameter: About 2.75 mm. Strength: Moderately strong. Aspect: Mostly erect. Texture and luster: Densely pubescent; matte. Color: Close to 152B.

*Pedicels*.—Length: About 2 mm. Diameter: About 0.5 mm. Strength: Moderately weak. Aspect: About 45° from peduncle axis. Texture and luster: Moderately to densely pubescent; matte. Color: Close to 144B.

*Reproductive organs*.—Stamens: Quantity per flower: Four. Filament length: About 1 cm. Filament color: Close to N74D. Anther shape: Elliptic; dorsifixed. Anther size: About 0.75 mm by 0.75 mm. Anther color: Close to N186A. Pollen amount: Moderate. Pollen color: Close to 155A. Pistils: Quantity per flower: One. Pistil length: About 2.1 cm. Stigma diameter: About 0.5 mm. Stigma shape: Cleft. Stigma color: Close to 70A. Style length: About 2 cm. Style color: Close to N74C. Ovary color: Close to 147D; towards the apex, close to 184A.

*Seeds and fruits*.—To date, seed and fruit production has not been observed on plants of the new *Agastache*.

Pathogen & pest resistance: To date, plants of the new *Agastache* have not been noted to be resistant to pathogens and pests common to *Agastache* plants.

Garden performance: Plants of the new *Agastache* have exhibited good garden performance, to tolerate temperatures ranging from −13° C. to about 40° C. and to be suitable for USDA Hardiness Zones 7 to 11.

It is claimed:

1. A new and distinct *Agastache* plant named 'Danish Delight' as illustrated and described.

* * * * *